United States Patent [19]

Sorensen

[11] Patent Number: 5,437,678
[45] Date of Patent: Aug. 1, 1995

[54] OPHTHALMIC LENS REMOVAL METHOD AND APPARATUS

[75] Inventor: John T. Sorensen, Costa Mesa, Calif.

[73] Assignee: Neomedix Corporation, Laguna Niguel, Calif.

[21] Appl. No.: 984,229

[22] Filed: Nov. 30, 1992

[51] Int. Cl.$^6$ .............................................. A61F 9/007
[52] U.S. Cl. .................................... 606/107; 606/170
[58] Field of Search ................................ 606/170, 107

[56] References Cited

U.S. PATENT DOCUMENTS

| | | |
|---|---|---|
| 3,818,913 | 6/1974 | Wallach ............................. 606/170 |
| 3,976,077 | 8/1976 | Kerfoot, Jr. . |
| 4,002,169 | 1/1977 | Cupler, II . |
| 4,061,146 | 12/1977 | Baehr et al. . |
| 4,167,944 | 9/1979 | Banko . |
| 4,289,131 | 9/1981 | Mueller . |
| 4,368,734 | 1/1983 | Banko ................................. 128/305 |
| 4,445,509 | 5/1984 | Auth . |
| 4,631,052 | 12/1986 | Kensey . |
| 4,646,736 | 3/1987 | Auth .................................... 606/170 |
| 4,681,106 | 7/1987 | Kensey et al. . |
| 4,700,705 | 10/1987 | Kensey et al. . |
| 4,770,174 | 9/1988 | Luckman et al. . |
| 4,811,735 | 3/1989 | Nash et al. . |
| 4,823,793 | 4/1989 | Angulo et al. . |
| 4,825,865 | 5/1989 | Zelman . |
| 5,057,098 | 10/1991 | Zelman . |
| 5,074,867 | 12/1991 | Wilk .................................... 606/128 |
| 5,133,729 | 7/1992 | Sjostrom . |
| 5,154,696 | 10/1992 | Shearing ............................. 606/107 |

FOREIGN PATENT DOCUMENTS

| | | |
|---|---|---|
| 0147192 | 7/1985 | European Pat. Off. . |
| 0286415 | 10/1988 | European Pat. Off. . |
| 0310685 | 4/1989 | European Pat. Off. . |
| 3801318 | 7/1989 | Germany . |
| 2239060 | 6/1991 | United Kingdom . |
| WO89/00834 | 2/1989 | WIPO . |
| WO9211816 | 7/1992 | WIPO . |

OTHER PUBLICATIONS

"The development and application of a new surgical device–the Endoscopic Liquidiser and Surgical Aspirator (ELSA)", K. T. Ison et al. 1989.
"Recanalization of Obstructed Arteries and a Flexible, Rotating tip Catheter", Kenneth R. Kensey MD, 1987.
Miller, F. J., Kensey, D. R., Nash, John E.; Experimental Percutaneous Gallstone Lithotripsy: Results in Swine, Radiology165: 387–389, 1987.
Phacotmesis—Distributed by Dr. Anis at May 1993 Conference of the American Society of Cataract and Refractive Surgery.

Primary Examiner—Tamara L. Graysay
Attorney, Agent, or Firm—Stetina Brunda & Buyan

[57] ABSTRACT

Apparatus for reducing the size of an object disposed in a generally closed fluid medium includes a handpiece having an axis extending from a housing at a proximal end to a probe at an opposing distal end. A reducer at the distal end of the probe is adapted for insertion into the fluid medium where it is rotatable to reduce in size the object. The reducer is configured to create a fluid flow in the fluid medium so that the handpiece can be maintained laterally and axially stationary while the object is moved by the fluid flow into contact with the reducer. An associated method includes the steps of rotating the rotary member at a speed sufficient to reduce the size of the object, and in a manner to produce a flow of the fluid sufficient to move the object into the rotary member.

33 Claims, 5 Drawing Sheets

OPHTHALMIC LENS REMOVAL METHOD AND APPARATUS

BACKGROUND OF THE INVENTION

1. Field of the Invention

This invention relates generally to apparatus and methods for removing ophthalmic lenses and more specifically for removing a cataractous ophthalmic lens for vision restoration.

2. Discussion of the Prior Art

The lens of a human eye is a crystalline, transparent biconvex intraocular tissue that helps bring rays of light to focus on the retina. The lens is enclosed in a lens capsule and consists of lens cortex, and lens nucleus. The lens capsule is an elastic bag enveloping the lens and is suspended by fine ligaments (zonule) attached to the ciliary muscles. These muscles radially stretch and relax the capsule thereby varying the optical characteristics of the enclosed lens to provide the desired focus for an image. This is commonly referred to as accommodation.

The lens cortex is a jelly-like portion of the crystalline lens, composed of a multiplicity of thin lens fibers that form the main body of the lens. The lens cortex is located between the denser inner nucleus and the elastic outer capsule. The lens nucleus is an optically defined-zone which is denser in the central position of the lens. This nucleus becomes even denser with age, eventually hardening and filling the entire lens. Additionally the lens may become opacified.

This opacity and cloudiness of the crystalline lens or its surrounding transparent membrane, commonly referred to as a cataract, may be congenital or may be caused by trauma, disease, or age. The cataractous lens obstructs the passage of light and tends to prevent the formation of a clear image on the retina.

Surgery currently is the only method of restoring vision in a patient blinded by cataracts. The surgical removal of the opacified lens becomes necessary when visual loss due to cataract becomes significant. The lost optical power is restored by a contact lens, aphakic spectacle, or intraocular lens.

The cataract has become one of the most significant and common causes of ocular disability and blindness in our aging population. Cataract procedure is currently the most frequent surgery performed for a person over the age of 65. There were 4 million (U.S.: 1.6 million; foreign: 2.4 million) cataract surgeries performed in 1991, a number which is growing at an annual rate of 5%.

The classic method of cataract surgery is the removal of the intact lens through a 7-10 mm incision and its replacement with an intraocular lens made from biocompatible polymers. This extracapsular cataract procedure restores vision but often causes post-operative complications resulting from the large incision, which include a prolonged healing process, increased trauma and astigmatism. Nevertheless, a majority of the current cataract procedures in the U.S. are performed using this intact extracapsular cataract removal technique.

More recently phacoemulsification devices, relying upon ultrasound, have been used for emulsifying the lens and removing it through a 3 millimeter incision in a shorter operative time. This technique provides easier rehabilitation and eliminates most of the post-operative complications resulting from the larger incision of conventional extracapsular cataract procedures.

For the phacoemulslification procedure, a 3 mm limbal incision is made about 45° to the iris plane allowing insertion of the instrument's tip into the anterior chamber in a direction almost parallel to the iris. Once the limbal incision has been made, the central part of the anterior capsule must be widely opened to facilitate emulsification of the lens nucleus and cortical clean-up, as well as to provide for an ideal intraocular lens placement in the sulcus of the posterior chamber.

Phacoemulsification can be performed in the anterior chamber or posterior chamber of the eye. In the case of anterior chamber phacoemulsification, the cataract lens is maneuvered into the anterior chamber where it is carved and removed from the chamber. This method is more traumatic to the endothelial layer of the cornea; however, it is an easier procedure for the surgeons to perform. Posterior chamber phacoemulsification consists of carving or shaving the central part of the lens while the lens is still in the capsule. This method is more difficult to perform due to the possibility of rupturing the posterior lens capsule and exposing the vitreous which fills the volume of the inner eyeball.

The phacoemulsification technique provides the advantages of a smaller incision, a stronger post operative globe which reduces astigmatism, better wound closure, lower trauma and earlier improvement in vision. However, the phacoemulsification procedure is contra-indicated for patients with dislocated cataract lens, a shallow anterior chamber, miotic pupils, low cornea-endothelial cell counts, or myope (a totally hard lens). The phacoemulsification technique also requires intense training in maneuvering the ultrasonic probe to carve the cataract lens nucleus. The energy can be destructive to the endothelial cells of the cornea ultimately resulting in complete degeneration. Due to these adverse circumstances, only about 45% of the U.S. surgeons currently prefer to use this phacoemulsification method over the conventional extracapsular method for cataract removal.

Use of phacoemulsification devices to perform endocapsular cataract removal has also been investigated. In such a procedure, the cataractous lens must be carved away while both the anterior and posterior sides of the capsule are left intact. The extreme difficulty associated with this procedure has limited its adoption so that only about 1% of the U.S. cataract removal procedures are performed using this endocapsular technique.

Currently, there remains a need for apparatus that provide for safe and effective endocapsular lens removal, and associated methods which are less time consuming and skill intensive.

SUMMARY OF THE INVENTION

In accordance with the present invention, lens removal is accomplished with a rotary device which requires an incision of only about one to three millimeters. This small incision minimizes the trauma to the patient and increases the speed of recovery. With the small size of the incision, the postoperative complications are also minimized.

A probe associated with the device includes a sheath which initially covers a rotatable tip during insertion of the probe. With the probe in place, this sheath can be retracted, exposing the rotary tip within the capsule. A saline solution can then be injected into the capsule facilitating separation of the lens from the walls of the capsule, a procedure commonly referred to as hydrodissection.

Of particular interest to the present invention is the configuration of the probe tip which functions as a sharp impeller as it creates a flow of fluid within the capsule. This fluid flow draws the lens toward the probe tip where it is reduced in size for ultimate removal from the capsule. Importantly, this configuration of the probe tip enables the procedure to function with the probe held substantially stationary within the capsule. There is no need for the surgeon to carefully manipulate the probe tip in order to perform the procedure, thus the potential risks associated with damaging the posterior lens capsule are avoided. Furthermore, lens reduction with the present invention is not limited by the hardness of the cataract lens, whereas cataract hardness limits the use of phacoemulsification apparatus of the prior art because of difficulty associated with carving out cataract lenses that are either too hard or too soft.

As the lens is reduced, the contents within the capsule become increasingly fludic and mobile, facilitating flow of the lens fragments into the rotating probe tip. Thus the ability of this device to draw unaffected lens material into the rotating tip increases as the procedure progresses. By merely placing the rotary tip probe in a single position within the capsule, rapid reduction of the contents of the capsule occurs without the need for tip position manipulations. The fragmented lens material is easily removed by subsequent use of a conventional irrigation-aspiration apparatus.

In a preferred method of the invention, endocapsular cataract removal is achieved leaving both the anterior and posterior sides of the capsule intact. This is particularly desirable as it allows the possibility of injecting a fluid lens material substitute directly into the capsule. An injected elastomeric replacement material can benefit the patient with a potential for restoring accommodation capability. Furthermore, the endocapsular procedure avoids any risk associated with damaging the endothelial cell lining of the cornea.

These and other features and advantages of the invention will be more apparent with the discussion of preferred embodiment and reference to the associated drawings.

DESCRIPTION OF THE DRAWINGS

FIG. 6b is a front elevation view of the probe tip illustrated in FIG. 6a;

FIG. 7 is a perspective view of the probe tip illustrated in FIG. 6a;

FIG. 9a–9c is a series of axial cross-section views of the ocular lens and removal system, illustrating various steps in a method associated with the present invention;

DESCRIPTION OF PREFERRED EMBODIMENTS AND BEST MODE OF THE INVENTION

Figure 1:
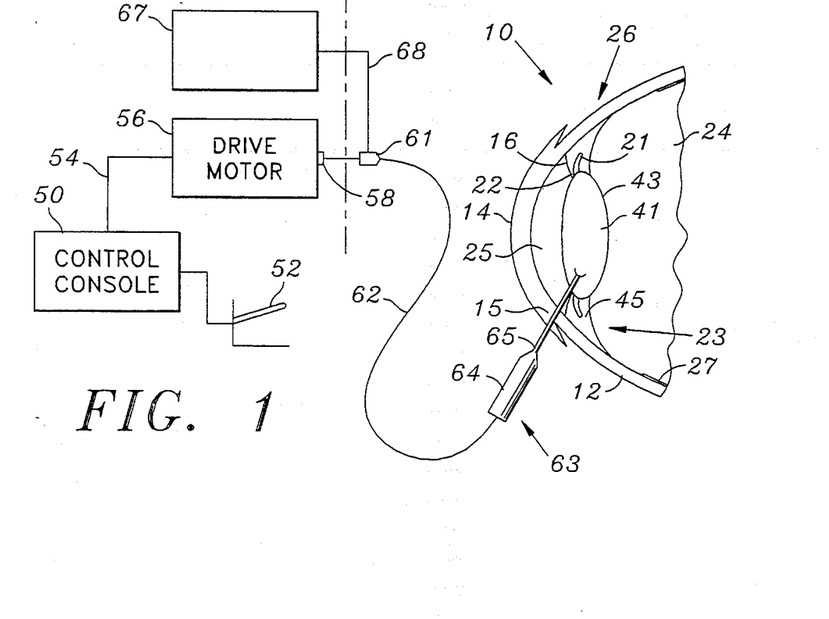
FIG. 1 is a cross-sectional view of an eye with the probe, in one aspect of the invention, operatively disposed to fragment the lens of the eye.

An eye is illustrated in FIG. 1 and designated generally by the reference numeral 10. The eye includes the sclera 12 and a cornea 14 which define an inner cavity of the eye 10. A limbus 15 provides a 1–2 mm wide transitional zone between the cornea 14 and the sclera 12. An iris 16 comprises a ring of pigmented tissue which lies behind the cornea 14. A central opening in the iris 16 is commonly referred to as a pupil 22. A lens structure 23 is supported by the sclera 12 and lies between the iris 16 and the vitreous 24, a transparent gelatinous mass which fills the interior of the eye 10 behind the lens structure 23. The interior of the eye 10 which lies between the cornea 14 and the vitreous 24 is divided into the two chambers, an anterior chamber 25 which lies between the cornea 14 and the plane of the iris 16, and a posterior chamber 26 which lies between the plane of the iris 16 and the vitreous 24.

When the eye 10 is functioning normally, an image passes through the cornea 14 and the pupil 22 where the lens structure 23 functions to form a focused image onto a retina 27 at the back of the vitreous 24. Electrical impulses are generated by the retina 27 and carried by an optic nerve (not shown) to the brain.

The lens structure 23 is of particular interest to the present invention. This structure includes a lens 41 which in its natural state is generally elastic and transparent. This lens 41 is enclosed in a lens capsule 43, the outer radius of which is supported by ciliary musculature 45. Under normal conditions, the ciliary musculature 45 responds to an image out of focus by radially stretching the lens capsule 43 or by relaxing the radial stretch on the lens capsule 43. This causes the enclosed lens 41 to vary its optical characteristics until the image is focused on the retina 27. Unfortunately, the aging process degrades the elasticity of the material forming the lens 41 so that accommodation becomes impaired as this ability of the eye to reshape the lens 41 decreases.

Another condition associated with aging is the clouding or reduced transparency of the crystalline material which forms the lens 41. When cataracts form in this manner, blindness typically results increasing the desirability of removing the cataractous lens to restore vision.

In one embodiment of the present invention, an apparatus for removing the lens 41 from the lens capsule 43 includes a control console 50 which houses a power supply and a motor controller that is operable by a foot pedal 52. Power from the control console 50 can be fed along a power cable 54 to a drive motor 56 which provides rotary power at a motor coupler 58. The motor controller in the console 50 can be adapted to provide for variations in speed as well as rotational direction. These characteristics of the rotary power controller can be programmed to provide desirable speed profiles, such as ramping, sine wave or square wave speed variation cycles.

This rotary power is introduced from the drive motor 56 through a drive cable connector 61 and drive cable 62 to a handpiece 63 which includes a housing 64 and a probe 65. When operatively disposed as illustrated, the probe 65 extends through a small incision in the limbus 15 of the eye 10 and into the lens capsule 43. The drive cable connector 61 may also be adapted to receive input from an irrigation-aspiration apparatus 67 through a tube 68.

In this particular embodiment of FIG. 1, the control console 50, drive motor 56, foot pedal 52 and irrigation apparatus 67 will generally be reusable in a non-sterile state. The drive cable connector 61, drive cable 62, and handpiece 63 can either be disposable or adapted for limited reuse. In either case, these elements typically will be utilized in a sterile state. Certainly a key advantage of this embodiment of the invention is that it facilitates implementation of a handpiece 63 which is smaller in size, lighter in weight and significantly more maneuverable than the handpieces associated with the phacoemulsification apparatus of the prior art.

In a further embodiment of the invention, the drive motor 56 is housed within and forms a portion of the control console 50. In this embodiment, the power cable 54 is foreshortened and exists only within the control console 50 such that the drive motor 56 and motor coupler 58 are integral with the control console 50.

Figure 2:
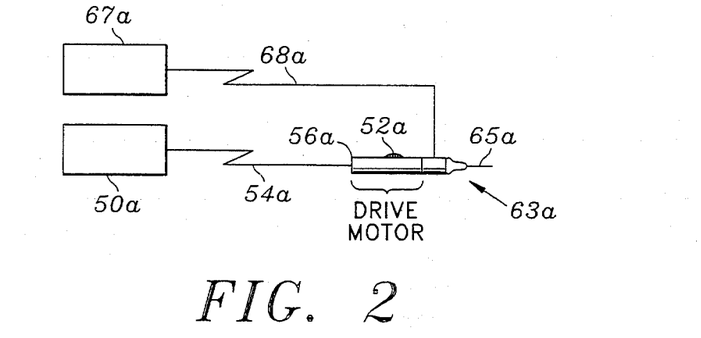
FIG. 2 is a side-elevation view of a further embodiment of the invention wherein a drive motor is configured as part of a handpiece.

A further embodiment of the invention is illustrated in FIG. 2 wherein the drive motor 56a forms a portion of the handpiece 63a. In this embodiment elements which are similar to those previously described are referred to with the same reference numeral followed by the lower case letter "a".

In the FIG. 2 embodiment, the power cable 54a extends between the control console 50a and drive motor 56a. In this case, however, the drive motor 56a is included in the handpiece 63a so the rotary drive cable (not shown) is foreshortened and exists only within the handpiece 63a. The foot pedal 52 may be replaced with a finger switch 52a. In this particular embodiment, the control console 50a will typically be reusable and will be utilized in a non-sterile state. The power cable 54a and motor drive 56a of the handpiece 63a may be adapted for limited reuse, but the distal end of the handpiece 63a, including the probe 65a, will typically be disposable. In this embodiment, the power cable 54a, drive motor 56a, and probe 65a will be utilized in a sterile state.

In either of the foregoing embodiments, the handpiece 63 will typically have a length between 10 cm and 20 cm with the probe 65 accounting for about 1 cm to 4 cm of that length. The outside diameter of the handpiece is preferably between 7 mm and 15 mm while the probe 65 has a diameter between about 3 F (1 mm) and 9 F (3 mm).

Figure 3A:
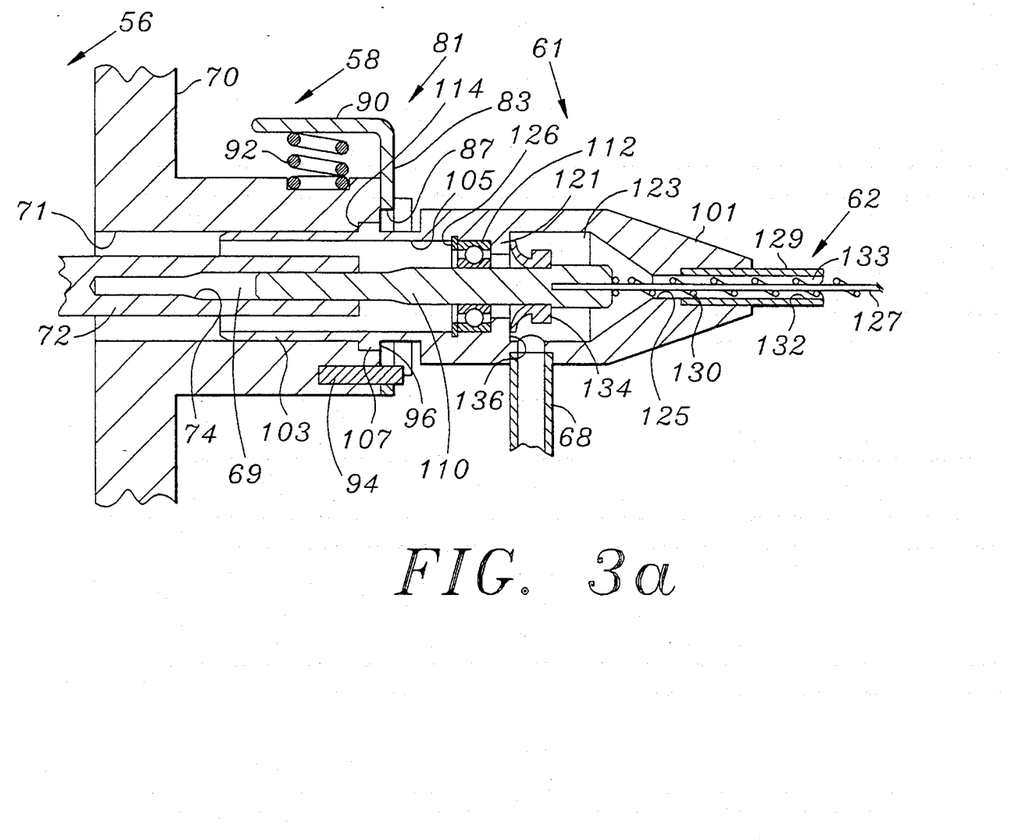
FIG. 3a is an axial cross-section view of a coupling between a drive motor and a drive cable connector associated with the present invention.

Of particular interest to the present invention are the drive cable connector 61, drive cable 62 and handpiece 63. These elements are coupled to the drive motor 56 by inserting the drive cable connector 61 into the motor coupler 58 along an axis 69 as illustrated in FIG. 3a.

In this particular embodiment, the drive motor 56 is located in an enclosure 70 having an inner bore 71 which extends through an annular projection forming the motor coupler 58. The drive motor 56 produces the rotary power which is provided to the motor coupler 58 on a rotary shaft 72. In order to provide a means for axial shaft engagement, this shaft 72 is provided with an axial bore 74 which is slotted or otherwise shaped to a non-circular configuration.

The motor coupler 58 is adapted to receive the drive cable connector 61 and to releasably lock the drive cable connector 61 in place, for example with a gate lock 81. In the illustrated embodiment the gate lock 81 includes a locking tab 83 which is slidably held in slots formed into the enclosure 70. The locking tab 83 is provided with an aperture 87 which is movable between a first position wherein the drive cable connector 61 can be inserted into or removed from the motor coupler 58, and a second position wherein the drive cable connector 61 is locked to the motor coupler 58. The locking tab 83 is provided with a thumb flange 90 which facilitates movement of the tab 83 between its first and second positions. The thumb flange 90 is also configured to compress a spring 92 against the enclosure 70. This spring 92 biases the flange 90 and locking tab 83 in the locking position as illustrated in FIG. 3A. A retaining pin 94 is fixed to the enclosure 70 and rides within a vertical slot 96 for limiting the distance of travel toward the locking position of the locking tab 83 when the drive cable connector 61 is absent.

The drive cable connector 61 includes a housing 101 which forms a cylindrical male fitting 103 which is configured to register with the inner bore 71 of the enclosure 70. This fitting 103 has an inner bore 105 and an outwardly extending annular locking flange 107. A drive cable connector shaft 110 is supported in a ball bearing 112 and is configured to register with the non-circular bore 74 of the motor coupler 58.

In operation, the locking tab 83 of the motor coupler 58 is initially depressed and the cylindrical fitting 103 is introduced through the aperture 87 into the inner bore 71 where the shaft 110 registers with the axial non-circular bore 74. The drive cable connector 61 is moved into the motor coupler 58 until the annular flange 107 engages a shoulder 114 on the enclosure 70. At this point the locking tab 83 can be released permitting the spring 92 to move the tab to the locking position. This movement causes the aperture 87 to engage the flange 107 and lock the drive cable connector 61 to the motor coupler 58.

The housing 101 of the drive cable connector 61 has walls which define an inwardly extending annular flange 121 and an inner cavity 123 which is tapered to an axial bore 125 at the distal end of the drive cable connector 61. The ball bearing 112 is located in the bore 105 and is held proximally of and against the flange 121 by a bearing retainer 126.

At the distal end of the drive cable connector 61 the rotary motion imparted to the shaft 110 is transferred to a flexible shaft or cable 127 which is supported within a flexible tube 129 by a helical bearing 130. In this embodiment, the flexible tube 129 has a lumen 132 with the same diameter as bore 125. The helical bearing 130 defines with the cable 127 and the flexible tube 129 a helical channel or passage 133 which extends from the drive cable connector 61 to the handpiece 63. The elements 127-130 form the rotary drive cable 62.

In a particular procedure it may be desirable to irrigate and/or aspirate the operative site. This is accomplished in one embodiment by connecting the irrigation-/aspiration apparatus 67 through the tubing 68 to the housing 101. In the illustrated embodiment, fluid from the apparatus 67 is introduced into the cavity 123 and is communicated through the helical passage 133 in the drive cable 62 to the handpiece 63 and the distal end of the probe 65.

It is particularly desirable that the irrigation/aspiration fluid be isolated from the drive motor 56. This is accomplished in the illustrated embodiment by providing a high speed rotary face seal 134 which presses against and forms a fluid tight seal with a distally facing radial surface 136 of the annular flange 121.

Figure 3B:
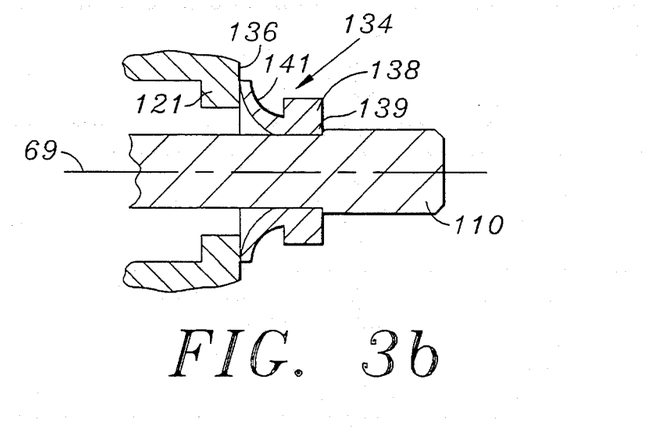
FIG. 3b is an enlarged axial cross-section view of a rotary seal associated with the drive cable connector.

The seal 134 is of particular interest to the present invention as shown in greater detail in FIG. 3b. In this embodiment, the seal 134 is a face seal formed from an elastomeric material and includes an enlarged generally cylindrical ring 138 which is seated against the flange 139 in a fixed relationship with the shaft 110. This ring 138 is integral with a skirt 141 which has a generally conical or frustoconical configuration and extends proximally into contact with the surface 136. The skirt 141 is highly compliant and extends increasingly radially outwardly with progressive positions in the proximal direction. The elastomeric characteristics of the seal 134 bias the skirt 141 into sealing engagement with the surface 136 of the flange 121.

With this configuration and orientation, the seal 134 functions as a high speed rotary seal, making it particularly advantageous for use in the lens removal system. With increasing speed of rotation, centrifugal force causes the skirt 141 to flare radially outwardly. This causes the pressure of the seal 134 against the surface 136 to decrease with an increasing speed of rotation. These characteristics of the seal 134 also reduce the frictional forces which might generate heat and otherwise impede high rotational speeds. A preferred embodiment of this seal is manufactured by Forsheda Shaft Seal Corporation and is referred to as a Forsheda V-ring seal.

Figure 4:
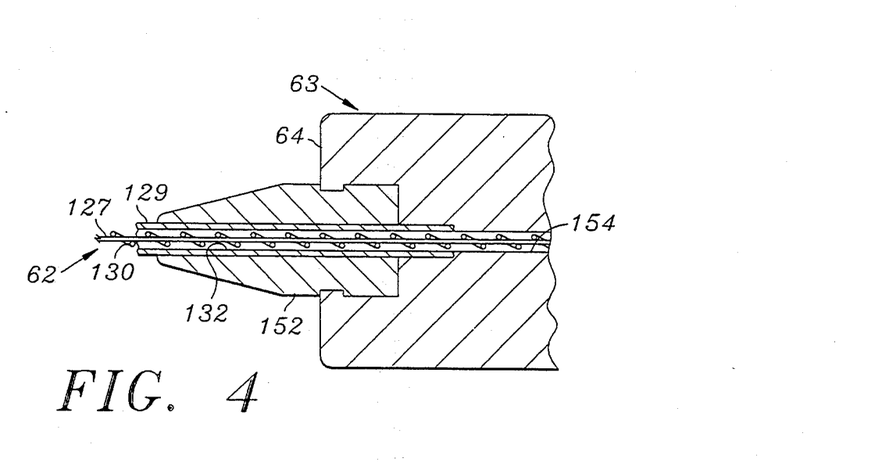
FIG. 4 is an axial cross-section view of a proximal end of the handpiece associated with the present invention.

At the opposite end of the rotary drive cable 62, the proximal end of the handpiece 63 is provided with an elastomeric strain relief member 152 as illustrated in FIG. 4. This member 152 is disposed around the drive cable 62 where it enters the housing 64 of the handpiece 63. Within the housing 64, the flexible tube 129 is terminated, but the drive cable 127 and helical bearing 130 continue through the housing 64 within a bore 154 with the same diameter as the lumen 132 of flexible tube 129.

Figure 5A:
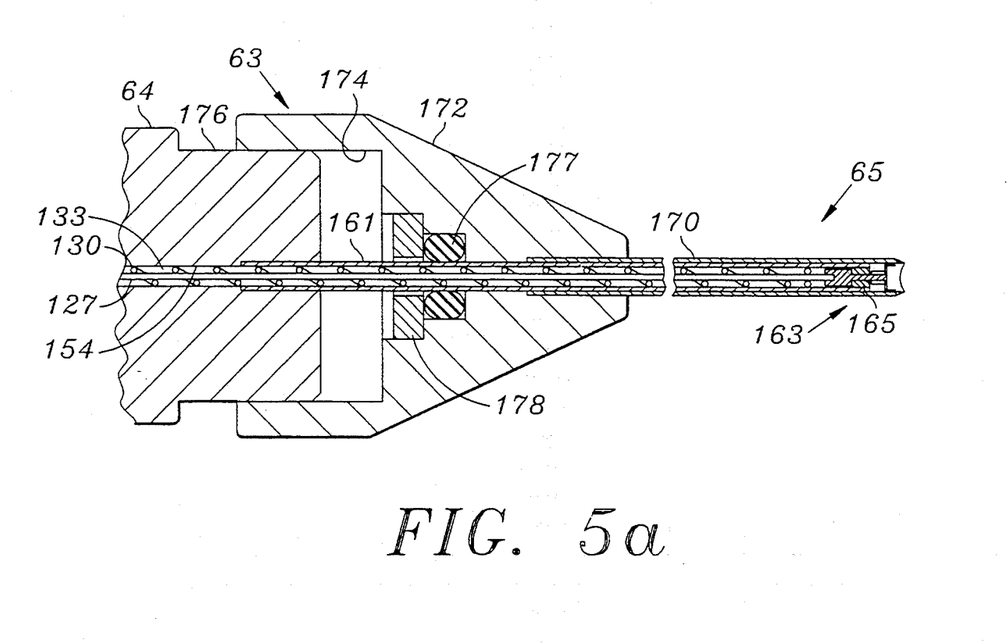
FIG. 5a is an axial cross-section view of a sheath disposed in a distal position to cover a rotary tip of the handpiece.

A preferred embodiment of the distal end of the handpiece 63 is illustrated in FIG. 5a. In this view, the probe 65 of the handpiece 63 is illustrated to include a cannula 161 which is fixed to the housing 64 and provides an extension of bore 154. The drive cable 127 and supporting helical bearing 130 and the helical fluid passage 133 extend into the cannula 161 to the distal end of the probe 65. In this distal location, the helical bearing 130 is terminated, and a rotary tip 163 is fixed to the drive cable 127 and supported by a bushing 165.

Figure 5B:
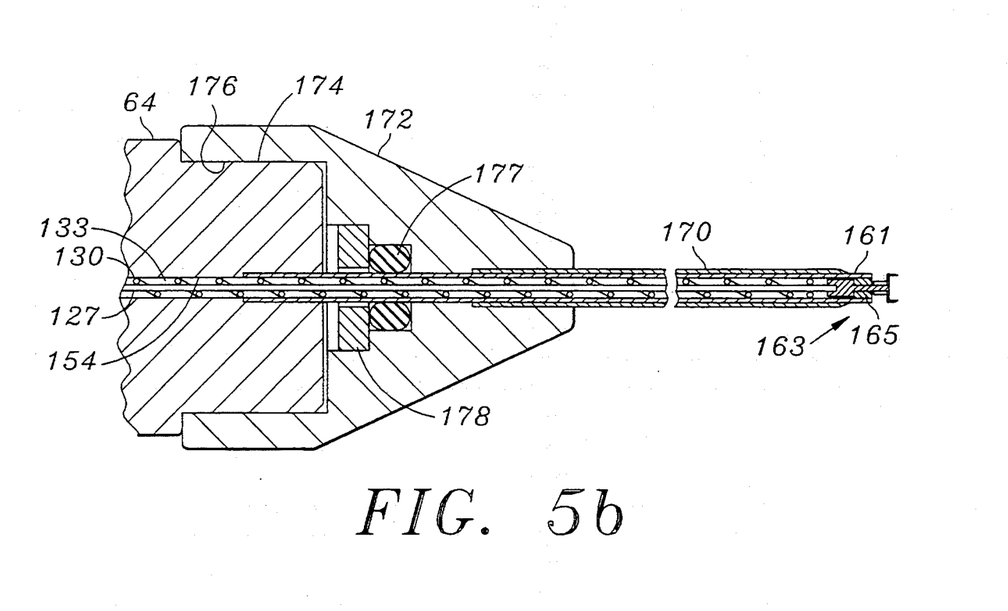
FIG. 5b is an axial cross-section view of the sheath disposed in a proximal position to expose the rotary tip.

In a preferred method associated with the invention the probe 65 is introduced into the lens capsule 43 with a needle structure. This is accomplished in the embodiment of FIG. 5a by providing an outer sheath 170 which is slidable relative to the cannula 161 and movable between a distal position wherein the rotary tip 163 is covered (as illustrated in FIG. 5a) and a proximal position wherein the rotary tip 163 is exposed (as illustrated in FIG. 5b).

The outer sheath 170 can be fixed to a nose cone 172 which is axially movable relative to the housing 64. In a preferred embodiment, the nose cone 172 includes a proximal bore 174 which registers with a cylindrical surface 176 which projects from the distal end of the housing 64. The nose cone 172 is configured to receive an O-ring 177 and associated retainer 178. The O-ring provides a seal between the cannula 161 and the sheath 170. This seal prevents air from entering the operative site and disrupting the induced fluid flow, for example, during aspiration or during activation of the rotary tip 163. This seal also prevents fluids from escaping from the operative site. The friction created between the nose cone 172 and cylindrical surface 176 as well as between the O-ring 177 and the cannula 161 may be sufficient to maintain the sheath 170 in either the forward or retracted position. In an embodiment including the nose cone 172, the distal end of the protective sheath 170 is preferably sharpened to facilitate puncture of the lens capsule 43 and entry into lens the 41.

Figure 6A:
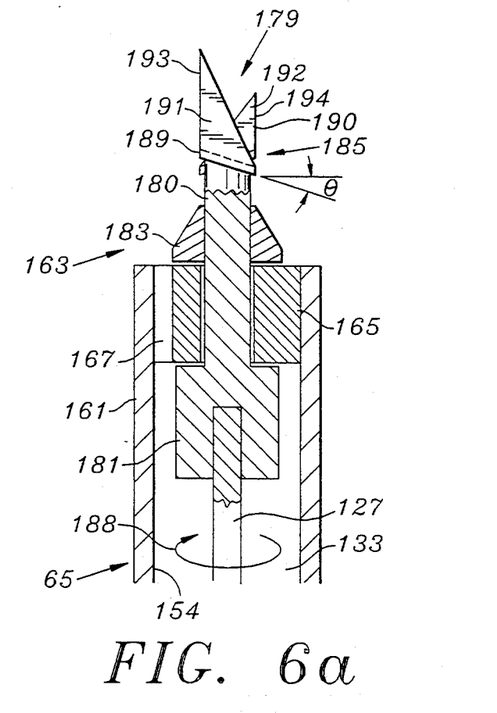
FIG. 6a is a side-elevation view of a preferred configuration of the probe tip having a single cross member.
Figure 6B:
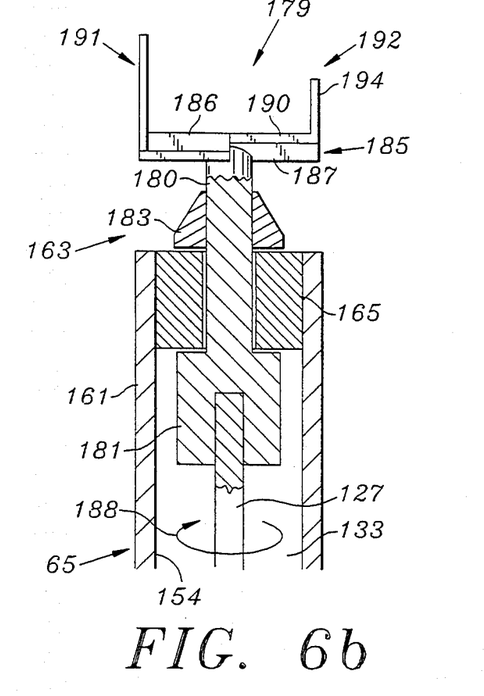

The configuration of the rotary tip 163 is best illustrated in FIGS. 6a and 6b to include a reducer 179 supported on a shaft 180 which has an enlargement 181 at its proximal end. This enlargement 181 is fixed to the end of the drive cable 127 within the cannula 161 and proximally of the bushing 165. Distally of the bushing 165 a spacer 183 can be provided in fixed relationship with the shaft 180 to secure the rotary tip 163 at the distal end of the probe 65. Fluid is communicated to the operative site through the passage 133 and one or more axial slots 167 in the bushing 165.

Figure 7:
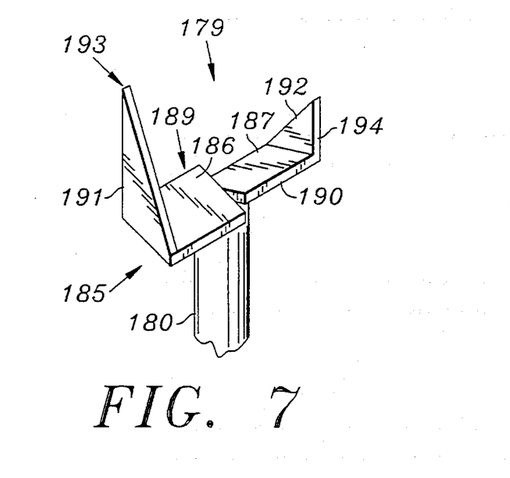

In a preferred embodiment the reducer 179 at the distal end of the rotary tip 163 includes a cross bar 185 which is fixed at its center transversely to the shaft 180 as illustrated in FIG. 7. On opposite sides of shaft 180, the cross bar 185 has opposing arms 186 and 187 which are pitched at an angle $\theta$ (best illustrated in FIG. 6) between 0° and 90°. When the shaft 180 is rotated, for example in the direction of arrow 188 in FIG. 6, the pitched arm 186 has a leading edge 189 and the pitched arm 187 has a leading edge 190.

With this configuration and orientation, the cross bar 185 functions as an impeller (in the form of a pitched blade turbine) which in a generally confined fluid environment will create a fluid flow of particular interest to the present invention. Rotation of the impeller induces three-dimensional fluid flow with axial, radial and tangential components. In the present invention, the axial flow component is of particular interest because it is primarily the axial component which draws the object to be reduced into contact with the reducer 179. The best compromise to induce the axial inflow desired for the present invention is in a range of pitch angles $\theta$ between 0° and 45°.

The reducer 179 can be provided with an axially extending member at each end of the cross bar 185. These axial members enhance the reducing action and are configured to be the first point of contact between the impeller and any object drawn into it by the fluid flow. The axial members, designated by the reference numerals 191 and 192 in FIG. 6 extend generally axially of the outer ends of the crossbar 185. The axial member 191 has a triangular configuration with a leading edge 193 which is disposed in a common axial plane with the leading edge 189. The axial member 192 can be similarly constructed but with a leading edge 194 which is shorter in axial length than the axial member 191. This axial member 192 has a triangular configuration which can be disposed in a common axial plane with the leading edge 190. The leading edges 189, 190, 193 and 194 are preferably sharpened to facilitate cutting or other reduction of the lens 41.

Figure 8:
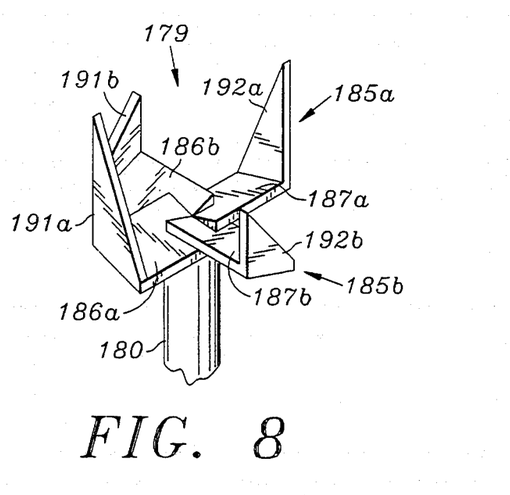
FIG. 8 is a perspective view of a probe tip having two cross members.

The reducer 179 illustrated in FIG. 8 includes two cross members 185a and 185b which are disposed in generally perpendicular relationship on the shaft 180. In this embodiment, the axial members 191a and 192a are disposed at opposite ends of the cross member 185a and are illustrated to be generally equal in axial dimension. A pair of axial members 191b and 192b are disposed at the ends of the cross member 185b and are also illustrated to be generally equal in axial dimension but shorter than the axial members 191a and 192a.

In order to achieve the desired fluid flow and speed of reduction, the pitched arms 186, 186a, 186b, 187, 187a, and 187b preferably have radial lengths of two to six times the radius of the shaft 180. The longer axial members 191, 191a, and 192a, have a preferred axial length about equal to the radial length of the pitched arms 186, 186a, 186b, 187, 187a, and 187b. The shorter axial members 192, 191b, and 192b preferably have an axial length of about one-half the axial length of the longer axial members 191, 191a, and 192a. In a preferred embodiment wherein the shaft 180 has a diameter of about 0.1 mm, the pitched arms 186 and 187 have a radial length of about 0.07 mm. The axial member 191 has an axial length of about 1.0 mm while the axial member 192 has an axial length of about 0.5 mm. The pitched arms 186 and 187 and axial members 191 and 192 are preferably formed of hardened stainless steel having a thickness of about 0.1 mm.

In the present invention, other embodiments of the reducer 179 would generally include any impeller which induces axial flow upon rotation. Such impellers may or may not be additionally modified to provide axially extending members to enhance the reducing action. Preferred embodiments of the reducer 179 are generally configured with one to six symmetrically or asymmetrically arranged pitched arms. Each of these pitched arms can either be radially oriented or inclined relative to the rotational axis.

The present method is intended for reducing in size an object disposed in a generally confined fluid medium environment within a living mammalian body. A rotary member is inserted into the fluid medium where the axis of rotation and axial position of the rotary member is maintained generally stationary. The rotary member is rotated at a speed sufficient to reduce the object when the object is moved into the rotary member. The rotary member may be positioned into the fluid medium environment either by locating the rotary member at the distal end of a probe or by suspending the rotary member in a magnetic field.

The method of the present invention is intended to be carried out in an environment wherein the probe 65 can be held generally stationary and a flow of fluid in the environment will bring material to the rotary tip 163 for reduction. This may be an environment where fluid flow already exists or it may be an environment which is sufficiently closed that the impeller action of the cross bar 185 will produce a generally continuous flow into the reducer 179. This flow will carry any object present in the environment into the reducer 179 for reduction in accordance with the present invention.

As used herein, the word "reducing" and derivatives thereof is deemed to include cutting, macerating, shearing, tearing, emulsifying, dissecting, fragmenting, and otherwise dividing objects within the environment. The reduction occurs when the object is in general contact with the reducer 179. This may include actual contact between the object and the reducer 179. However, it is also deemed to include those instances where there is no actual contact but sufficient proximity between the object and the reducer 179 for the desired reduction to occur.

Figures 9A, 9B:
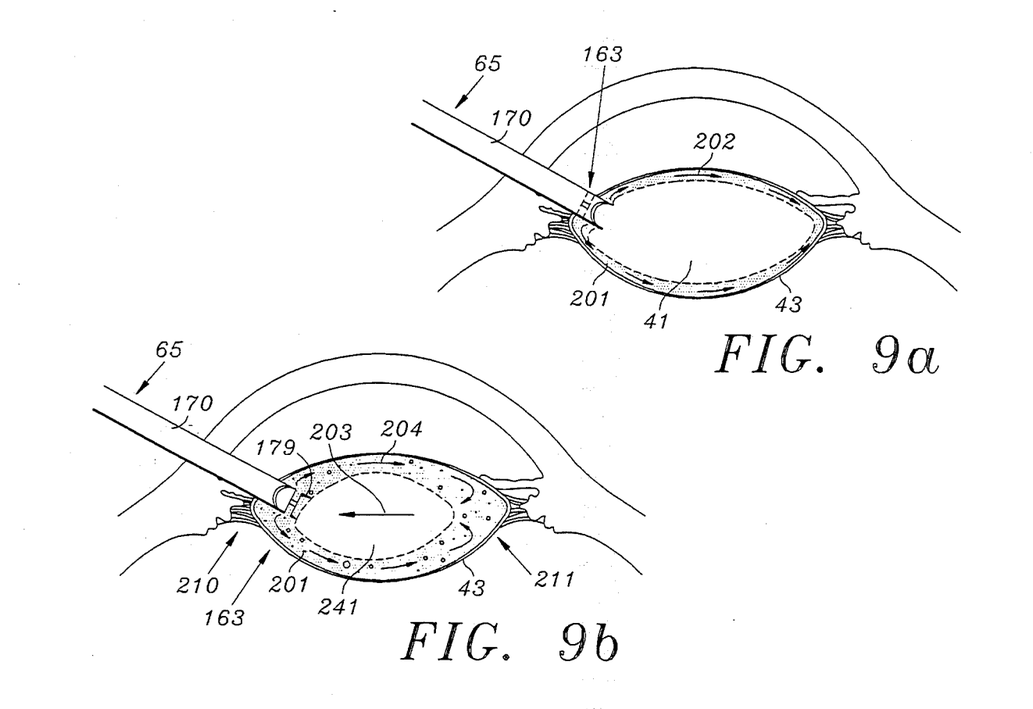
FIG. 9a illustrates a step for inserting the probe and injecting a liquid to effect hydrodissection.
FIG. 9b illustrates a step for creating an enclosed fluid flow for moving the lens into the rotating tip of a stationary probe.

The apparatus previously discussed is particularly useful in a method for removing the lens 41 from the lens capsule 43. In an initial step of the method, the sheath 170 described with reference to FIG. 5 is moved to its forward or distal position covering the rotary tip 163 as shown in FIG. 5a. In this position, the sharp distal end of the sheath 170 is exposed to facilitate introduction of the probe 65 through the anterior side of the lens capsule 43. With the probe 65 in this position, as illustrated in FIG. 9a, a liquid 201, such as a saline solution, can be introduced through the probe 65 into the lens capsule 43. As the liquid 201 is introduced, the liquid will flow along the interior surfaces of the lens capsule 43 causing a separation of the lens capsule 43 from the lens 41. The method of separating the lens capsule from the lens by liquid injection is generally referred to as hydrodissection.

This hydrodissection is of particular interest to the present invention as it initially functions to increase the mobility of the lens 41 within the lens capsule 43. The injected liquid 201 also facilitates disposition of lens 41 in a liquid environment within the lens capsule 43. In addition, introduction of liquid 201 can facilitate hydration and softening of the outer regions (lens cortex) of the lens 41. The flow of the liquid 201 is illustrated by the arrows 202 in FIG. 9a.

The sheath 170 can be returned to its proximal position as illustrated in FIG. 5b either during or following the injection step. With the sheath 170 retracted, the rotary tip 163 is exposed.

As the foot pedal 52 is depressed, the control console 50 activates the drive motor 56 and imparts rotary motion through the drive cable 62 to the rotary tip 163. As the rotary tip 163 rotates, the reducer 179 begins to function as an impeller creating a fluid flow within the lens capsule 43. As the lens 41 moves into contact with the rotary tip 163, it is rapidly reduced into very small pieces. In the case of the lens 41, the outer portions may be particularly soft in which case they will preferentially tend to liquify under the high speed reducing action. In this manner, the initial reducing of the lens 41 tends to increase the amount of liquid within the capsule 43 subsequently enhancing the mobility of the unreduced lens under the fluid action created by the rotary tip 163.

Of particular importance to the present invention is the fact that the handpiece 63 and probe 65 can be held generally stationary within the lens capsule 43. There is no need to "search" with the probe 65 in order to reach the lens 41. Consequently, the likelihood of puncturing the lens capsule 43 by inadvertently over-extending the "reach" of the probe 65 is eliminated. This is a major advantage of the present invention over the prior art of phacoemulsification because a high degree of surgical skill and training is not required. Furthermore, the likelihood of tearing the lens capsule 43 at the point of probe entry as a result of probe manipulations, is greatly reduced.

As illustrated in FIG. 9b the probe can be held stationary while activation of the rotary tip 163 causes fluid flow as indicated by arrows 204 to move the unreduced portion of the lens 41 into the reducer 179. This movement of the unreduced lens 41 into the stationary probe 65 is illustrated by arrow 203 in FIG. 9b. As reduction of the lens 41 increases, the contents of the capsule 43 become increasingly fluidic and mobile. The axial inflow of fluid associated with this invention acts to draw into the probe 65 the unreduced portions of the lens 41, hereinafter designated by the reference numeral 241. In addition, the discharge of fluid from the reducer 179 reverses axial direction at a proximal end 210 of the lens capsule 43, flows along the lens capsule 43, and again reverses axial direction at a distal end 211 of the lens capsule 43, thus acting to push the unreduced portions of the lens 241 into the probe 65 as a result of the flow recirculation. Thus rotation of the reducer 179 functions to create a fluid flow within a relatively confined environment which moves the object to be reduced into the rotating reducer 179.

Figures 9C, 9D:
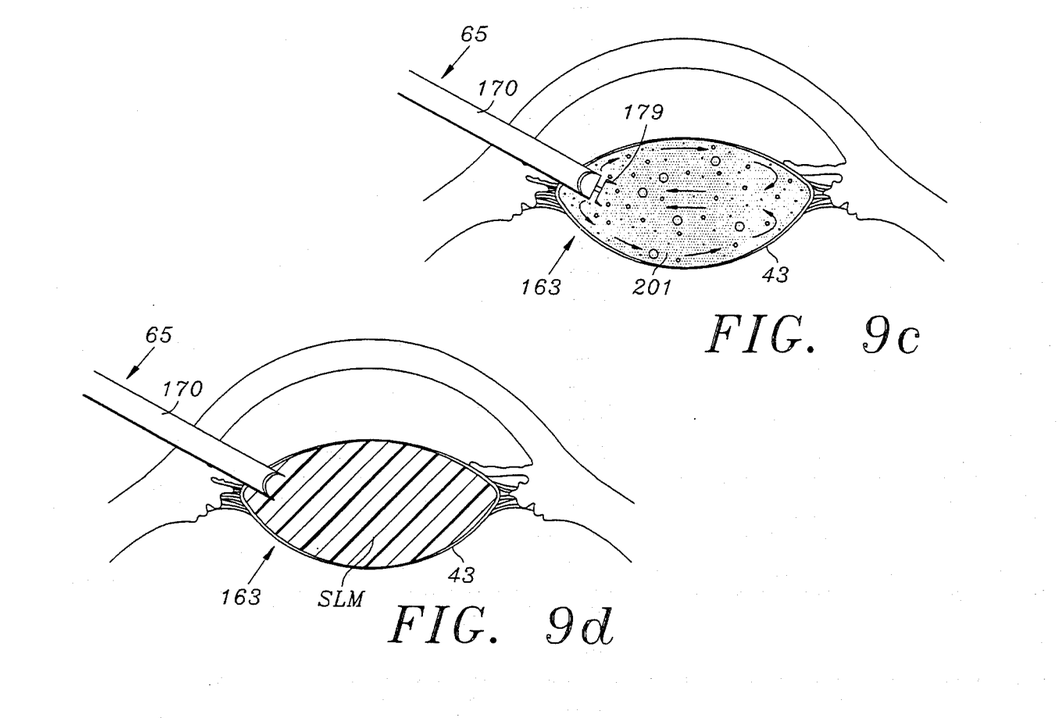
FIG. 9c illustrates an advanced step of lens fragmentation wherein the fluid flow is greatly increased and the lens is substantially fragmented for ultimate removal from the capsule.
FIG. 9d illustrates a step whereby a synthetic lens replacement material is introduced into the lens capsule following removal of the endogenous ophthalmic lens therefrom.

As reduction progresses, the lens 41 is completely reduced to small pieces as shown in FIG. 9c. The pieces of reduced lens material are of sufficiently small in size to be easily removed from the intact lens capsule 43 by aspiration. During the reduction process, it may be desirable to alter the fluidic properties within the confined environment by adding a second fluid or by exchanging the existing fluid with the second fluid.

As reduction progresses, or after it has been completed, the fluid and lens remnants within the capsule 43 can be aspirated through the probe 65 or through a separate probe (not shown) leaving the capsule 43 generally intact but absent the previously enclosed lens 41. In another embodiment, by retracting all inner workings from the outer sheath 170 of probe 65, the outer sheath 170 may provide a convenient means for aspiration of the fluid or may provide a means by which a separate probe can be introduced for aspiration. FIG. 9c shows completion of lens reduction such that the remnants of lens are sufficiently reduced in size to allow for their removal from the intact lens capsule 43 by aspiration/irrigation.

At this point, the steps associated with the method of the invention may differ considerably. Methods practiced in the prior art commonly include implantation of a synthetic intraocular lens substitute, or to correct vision with glasses or contact lenses in the absence of an implanted lens substitute. In one additional method, a synthetic lens material (SLM) can be injected into the lens capsule 43. This material fills the lens capsule 43 and essentially replaces the prior lens 41. An advantage of the endocapsular procedure of the present invention is that the lens capsule 43 is left intact during the lens removal operation so that it can still function as an enclosure for the injected lens material.

If a synthetic lens material is to be introduced into the lens capsule 43, such injection can occur through the probe 65 or it can be accomplished by a separate probe (not shown). In either case, the method will not be complete until the probe 65 is removed from the lens capsule 43. This is accomplished in a preferred method by moving the sheath 170 to its distal position thereby covering the rotary tip 163 as illustrated in FIG. 5a. In this configuration, the probe 65 can easily be retracted from the capsule 43 and the eye 10.

The speed of rotation of the reducer 179 is of particular interest to the present invention since it not only provides the fluid flow but also produces the desired reduction of the lens 41. The most desirable speed will of course depend upon the size and configuration of the reducer 179, the volume and shape of the generally confined environment, the viscosity of the fluid, the magnitude of fluid flow desired, and of course the speed of reduction desired. Other factors might include the hardness of the object being reduced. Speeds in a range between 10,000 and 300,000 rpm seem to provide the best compromise of these factors. A preferred range of speed for the lens removal process is 30,000 to 100,000 rpm.

When one is operating in these speed ranges, high friction forces and heat can develop unless these factors are adequately addressed. It is for this reason that the preferred embodiment includes the helical bearings 130 to support the cable 127 in the rotary drive cable 62. This bearing provides minimal contact with the cable 127 while at the same time providing support along its entire length. Particularly if the helical bearing is formed by a wire having a circular cross section, the contact between the helical wire bearing 130 and the cable 127 is along a helical line which provides for minimal contact support from the drive cable connector 61, through the handpiece 63, to the distal end of the probe 65.

Many variations on this concept will now be apparent to those skilled in the art. By way of example, the rotary member of the present invention need not be mechanically supported on the tip of a handpiece probe, but can be made of a magnetic material and suspended in the fluid environment by a magnetic field. The magnetic field can then be manipulated such that the rotary member remains generally laterally and axially stationary. Rotation of the rotary member on its rotational axis causes material within the fluid environment to be drawn by fluid flow to the rotary member where it is rapidly reduced.

By way of further example, material within the fluid environment drawn to the tip of a handpiece probe need not be reduced by direct mechanical interaction with the rotary member. In some cases, rotation of the rotary member on the tip of a handpiece probe can be used to induce a fluid flow that draws the material into proximity with the probe tip where a secondary energy source, such as laser, ultrasound, or electrohydraulic shock waves, can be utilized to effect reduction of the material.

Given these wide variations, which are all within the scope of this concept, one is cautioned not to restrict the invention to the embodiments which have been specifically disclosed and illustrated, but rather encouraged to determine the scope of the invention only with reference to the following claims.

I claim:

1. Apparatus for endocapsular reduction of the lens of a mammalian eye, the apparatus comprising:

a handpiece having an axis extending between a proximal end and an opposing distal end of the handpiece;

an elongate tubular housing included in the handpiece and disposed at the proximal end of the handpiece;

a probe included in the handpiece and extending from the housing to the distal end of the handpiece, the probe being adapted for insertion into the lens capsule;

a shaft rotatable within the tubular housing and extending through the probe to the distal end of the handpiece;

bearing means for supporting said shaft within the housing along at least one line of contact, said bearing means creating a channel extending along the probe;

a V-ring face seal positioned within said housing in contact with said shaft for sealing said channel;

reducing means coupled to the shaft at the distal end of the handpiece for reducing the object when the object is in general contact with the reducing means; and the reducing means being configured to create a fluid flow within the lens capsule to move the lens into contact with the lens reducing means.

2. The apparatus recited in claim 1 wherein the line of contact is helical.

3. The apparatus recited in claim 1 wherein the channel is helical.

4. The apparatus recited in claim 1 wherein the reducing means includes a tip coupled to the shaft and rotatable with the shaft to create the fluid flow.

5. A surgical reducer for endocapsular reduction of the lens of a mammalian eye, comprising:

a probe having an axis extending between a proximal end and an opposing distal end;

an elongate tubular housing included in the probe, the housing having a generally cylindrical inner surface including a particular surface extending generally radially of the axis;

a shaft rotatable within the tubular housing and extending to the distal end of the probe;

means rotatable with the shaft to create a force against the particular surface for forming a seal with the particular surface, the force having a magnitude which decreases with increasing rotation of the shaft;

a cutting tip coupled to the shaft at the distal end of the probe and tip shielding means disposed about said probe such that said cutting tip may be alternately (a) covered by said shielding means to facilitate introduction of the probe through the lens capsule, and (b) protruding outside of said shielding means such that said cutting tip may contact and reduce lens matter within said lens capsule.

6. The surgical reducer recited in claim 5 wherein the seal means comprises:

a ring member fixed to the shaft in proximity to the particular surface;

a skirt rotatable with the ring member and biased to seat on the particular surface to create the seal; and the skirt moving radially outwardly away from the particular surface in response to rotation of the shaft, the ring member and the skirt to decrease the sealing force at higher velocities of rotation.

7. The surgical reducer recited in claim 6 wherein the skirt is generally frustraconical in shape.

8. The surgical reducer recited in claim 7 wherein the skirt is annular and extends radially outwardly with progressive positions from the ring member to the particular surface.

9. The surgical reducer recited in claim 5 further comprising a sheath disposed over the probe and having a sharp distal end which is axially retractable to expose the cutting tip.

10. The surgical reducer recited in claim 5 wherein the cutting tip has the configuration of a pitched blade turbine.

11. A surgical reducer for reducing and removing the lens of a mammalian eye, comprising:

a power controller providing a power signal on a power line;

a drive motor coupled to the power line and responsive to the power signal to provide rotary power;

a handpiece;

a housing included in the handpiece and receiving the rotary power from the drive motor;

a probe included in the handpiece and extending from the housing to a rotary lens reducing tip;

means for defining a channel between the drive motor and the probe;

a drive shaft disposed in the channel for conveying the rotary power to the tip of the probe;

means for introducing a fluid through the channel to the rotary tip of the probe;

means fixed to the drive shaft for sealing the channel; and tip shielding means disposed about said probe such that said lens reducing tip may be alternately a) covered by said shielding means to facilitate introduction of the probe through the lens capsule, and b) protruding outside of said shielding means so as to contact and reduce said lens within said lens capsule.

12. The reducer recited in claim 11 wherein the drive motor is disposed in the housing of the handpiece.

13. The reducer recited in claim 11 further comprising:

a drive cable disposed between the drive motor and the handpiece;

a connector disposed to couple the cable to the drive motor; and a face seal included in the sealing means and disposed in the connector.

14. The surgical reducer recited in claim 13 wherein said drive shaft has a longitudinal axis extending therethrough and wherein;

the connector includes a housing having a generally cylindrical inner surface and a radial surface generally perpendicular to said longitudinal axis of said drive shaft; and the face seal includes a skirt rotatable with the shaft to form the seal with the radial surface.

15. The surgical reducer recited in claim 13 the housing of the connector is integral with the housing of the handpiece.

16. A method for endocapsular reduction and removal of a lens from a mammalian eye, said method comprising the steps of:

A) providing a rotary lens reducing device, said device comprising:

i) a rotating head member;

ii) a protective sheath sized and configured to cover said rotating head member, said sheath being alternately moveable, relative to said rotating head member, between:

a) a first position whereat said rotating head is covered by said protective sheath; and b) a second position whereat said rotating head protrudes out of said protective sheath;

iii) said rotating head being configured such that, when held in a substantially stationary position within the lens capsule, and rotated at sufficient velocity, said rotating head will concomitantly i) reduce lens matter which comes into contact with said head and ii) draw a flow of fluid toward said rotating head so as to cause the entire lens to be drawn into contact with the stationarily positioned rotating head;

B) initially positioning the tubular sheath of said device in said first position;

C) inserting the distal end of said tubular sheath into the lens capsule;

D) moving the tubular sheath of said device to said second position, thereby causing said rotary head to become exposed within said lens capsule;

E) maintaining said device such that said rotating head member remains in a axially stationary position;

F) causing said rotating head to rotate at sufficient velocity to effect complete reduction of the lens while said device remains in said substantially stationary position;

G) removing the reduced lens matter from the interior of the lens capsule;

H) returning said tubular sheath to said first position; and

I) extracting the rotary lens reducing device from the eye.

17. The method of claim 16 further comprising the step of:

J) instilling a lens-replacement material into the lens capsule following removal of the reduced lens matter therefrom.

18. The method of claim 17 wherein step J comprises:
injecting a synthetic lens replacement material into the lens capsule.

19. The method of claim 16 wherein the distal end of said protective sheath is sharpened and wherein step C comprises:
advancing the sharpened distal end of said protective sheath through the lens capsule.

20. The method of claim 16 wherein step F comprises:
rotating said rotary head at a rotational velocity in the range of 10,000–300,000 RPM.

21. The method of claim 16 wherein step F comprises:
rotating said rotary head at a rotational velocity in the range of 30,000–100,000 RPM.

22. The method of claim 16 wherein step G further comprises:
concomitantly removing reduced lens matter from the interior of the lens capsule by simultaneously infusing an inflow of liquid into the lens capsule while withdrawing liquid and reduced lens matter out from the lens capsule.

23. A device for reducing a cataract-affected lens within the lens capsule of a mammalian eye, said device comprising:
a rotatable shaft;
a rotating lens reducing and fluid-flow generating head mounted on said rotatable shaft, said head being configured such that, when rotated at sufficient velocity and held in a substantially stationary position within the lens capsule of the eye, the rotation of said head will reduce lens matter coming into contact therewith while concomitantly drawing a flow of fluid toward said head;
said head comprising an impeller configured to cause the entire lens to be drawn into contact with said head while said head remains in said substantially stationary position within the lens capsule;
a protective sheath mounted on said device and alternately positionable relative to said rotating head between:

i) a first position wherein said rotating head is covered by said sheath; and ii) a second position wherein said rotating head protrudes outside of said sheath.

24. The device of claim 23 wherein said rotating lens reducing and fluid flow generating head comprises:
at least one impeller blade extending from said shaft, said at least one impeller blade having a pitch angle which induces said flow of fluid and draws the lens into contact with the rotating lens reducing and fluid-flow-generating head.

25. The device of claim 23 wherein said rotating lens reducing and fluid-flow-generating head comprises:
at least one cross member disposed in generally perpendicular relationship to said shaft and an axial member extending from said cross member.

26. The device of claim 23 further comprising:
a rotational drive source operative to rotate said shaft.

27. The device of claim 26 wherein said rotational drive source is operative to rotate said shaft and said rotating head at a velocity within the range of 10,000–300,000 RPM.

28. The device of claim 26 wherein said rotational drive source is operative to rotate said shaft and said rotating head at a velocity within the range of 30,000–100,000 RPM.

29. The device of claim 26 further comprising:
a rotational drive cable connecting said rotary drive source to said rotational shaft.

30. The device of claim 23 further comprising:
a hand piece sized and configured to be grasped by the human hand; and
said rotatable shaft having said rotating head mounted thereon extending from said hand piece such that the portion of said device incorporating said rotating head may be inserted into the lens capsule while the hand piece is held in a human hand.

31. The device of claim 23 wherein said protective sheath comprises a tubular member having a distal end, a proximal end and a hollow inner bore, said tubular member being positioned about at least a portion of said rotatable shaft and longitudinally moveable between:

i) a first position wherein said rotating head is housed substantially within the bore of said tubular member; and ii) a second position wherein said rotating head protrudes at least partially out of and beyond the distal end of said tubular member.

32. The device of claim 31 wherein the distal end of said tubular member is sharpened such that, when said tubular member is positioned in said first position with said rotary head housed within the bore thereof, the sharpened distal end of said tubular member may be passed through the lens capsule and, subsequently, said tubular member may be shifted to said second position such that the rotating distal head member of the device is unconcealed by the tubular member and operatively positioned within the lens capsule to effect reduction of the lens matter contained therewithin.

33. The device of claim 31 wherein said tubular member has an elongate, cylindrical outer surface and is sized and configured to be insertable, distal end first, into the lens capsule of the mammalian eye.

* * * * *